(12) United States Patent
Meridew et al.

(10) Patent No.: US 7,713,300 B2
(45) Date of Patent: May 11, 2010

(54) APPARATUS AND METHOD FOR MANIPULATING A FLEXIBLE STRAND AND SOFT TISSUE REPLACEMENT DURING SURGERY

(75) Inventors: Jason D Meridew, Syracuse, IN (US); Troy M Walters, Plymouth, IN (US); Ryan A Kaiser, Leesburg, IN (US)

(73) Assignee: Biomet Sports Medicince, LLC, Warsaw, IN (US)

( * ) Notice: Subject to any disclaimer, the term of this patent is extended or adjusted under 35 U.S.C. 154(b) by 1041 days.

(21) Appl. No.: 11/384,988

(22) Filed: Mar. 20, 2006

(65) Prior Publication Data

US 2006/0173465 A1    Aug. 3, 2006

Related U.S. Application Data

(63) Continuation-in-part of application No. 10/066,519, filed on Jan. 31, 2002, now Pat. No. 7,033,364.

(51) Int. Cl.
*A61F 2/08* (2006.01)
*A61F 2/30* (2006.01)

(52) U.S. Cl. .............. 623/13.14; 623/13.11; 623/13.12; 606/65

(58) Field of Classification Search ... 623/13.11–13.14; 606/65
See application file for complete search history.

(56) References Cited

U.S. PATENT DOCUMENTS

| | | | |
|---|---|---|---|
| 2,695,607 A | 11/1954 | Hipps et al. |
| 3,871,379 A | 3/1975 | Clarke |
| D249,705 S | 9/1978 | London |
| 4,257,411 A | 3/1981 | Cho |
| 4,535,768 A | 8/1985 | Hourahane et al. |
| 4,922,897 A | 5/1990 | Sapega et al. |
| 4,985,032 A | 1/1991 | Goble |
| 4,998,937 A | 3/1991 | Grimes |
| 5,004,474 A | 4/1991 | Fronk et al. |
| 5,030,219 A | 7/1991 | Matsen, III et al. |
| 5,098,435 A | 3/1992 | Stednitz et al. |
| 5,108,396 A | 4/1992 | Lackey et al. |
| 5,112,336 A | 5/1992 | Krevolin et al. |
| 5,129,902 A | 7/1992 | Goble et al. |
| 5,201,744 A | 4/1993 | Jones |
| 5,234,434 A | 8/1993 | Goble et al. |
| 5,234,444 A | 8/1993 | Christoudias |
| 5,257,996 A | 11/1993 | McGuire |
| 5,266,075 A | 11/1993 | Clark et al. |
| 5,300,077 A | 4/1994 | Howell |
| 5,350,380 A | 9/1994 | Goble et al. |

(Continued)

FOREIGN PATENT DOCUMENTS

EP       1 360 949       11/2003

(Continued)

*Primary Examiner*—Thomas J Sweet
*Assistant Examiner*—Yashita Sharma
(74) *Attorney, Agent, or Firm*—Harness, Dickey

(57) ABSTRACT

An apparatus and method is disclosed for performing a surgery, such as an orthopedic surgery. The apparatus can include a guide portion and an alignment portion. The guide portion can assist in positioning the alignment portion to assist in aligning an implant. The implant can be aligned and positioned to hold a graft relative to a bone portion.

24 Claims, 11 Drawing Sheets

U.S. PATENT DOCUMENTS

| | | | |
|---|---|---|---|
| 5,354,300 A | 10/1994 | Goble et al. |
| 5,356,413 A | 10/1994 | Martins et al. |
| 5,393,302 A | 2/1995 | Clark et al. |
| 5,397,356 A | 3/1995 | Goble et al. |
| D357,534 S | 4/1995 | Hayes |
| 5,423,823 A | 6/1995 | Schmieding |
| 5,431,651 A | 7/1995 | Goble |
| 5,437,677 A | 8/1995 | Shearer et al. |
| 5,454,365 A | 10/1995 | Bonutti |
| 5,562,671 A | 10/1996 | Goble et al. |
| 5,601,562 A | 2/1997 | Wolf et al. |
| 5,643,273 A | 7/1997 | Clark |
| 5,674,224 A | 10/1997 | Howell et al. |
| 5,849,013 A | 12/1998 | Whittaker et al. |
| 5,891,150 A | 4/1999 | Chan |
| 5,895,425 A | 4/1999 | Grafton et al. |
| 5,918,604 A | 7/1999 | Whelan |
| 5,931,839 A | 8/1999 | Medoff |
| 6,039,739 A | 3/2000 | Simon |
| 6,066,173 A | 5/2000 | McKernan et al. |
| 6,110,211 A | 8/2000 | Weiss |
| 6,113,604 A | 9/2000 | Whittaker et al. |
| 6,132,433 A | 10/2000 | Whelan |
| 6,231,611 B1 | 5/2001 | Mosseri |
| 6,306,138 B1 * | 10/2001 | Clark et al. ............. 606/65 |
| 6,325,804 B1 | 12/2001 | Wenstrom, Jr. et al. |
| 6,342,056 B1 | 1/2002 | Mac-Thiong et al. |
| 6,371,124 B1 | 4/2002 | Whelan |
| 6,375,684 B1 | 4/2002 | Kriek |
| 6,379,384 B1 | 4/2002 | McKernan et al. |
| 6,494,913 B1 | 12/2002 | Huebner |
| 6,497,726 B1 | 12/2002 | Carter et al. |
| 6,517,546 B2 | 2/2003 | Whittaker et al. |
| 6,537,319 B2 | 3/2003 | Whelan |
| 6,562,071 B2 | 5/2003 | Jarvinen |
| 6,589,281 B2 | 7/2003 | Hyde, Jr. |
| 6,673,115 B2 | 1/2004 | Resch et al. |
| 6,712,823 B2 | 3/2004 | Terrill-Grisoni et al. |
| 6,712,849 B2 * | 3/2004 | Re et al. ............. 623/13.14 |
| 6,733,529 B2 | 5/2004 | Whelan |
| 6,752,830 B1 | 6/2004 | Goble et al. |
| 2001/0047210 A1 | 11/2001 | Wolf |
| 2001/0053934 A1 | 12/2001 | Schmieding |
| 2002/0019635 A1 | 2/2002 | Wenstrom, Jr. et al. |
| 2002/0087160 A1 | 7/2002 | Clark et al. |
| 2002/0099381 A1 | 7/2002 | Maroney |
| 2002/0111689 A1 | 8/2002 | Hyde, Jr. |
| 2002/0111690 A1 | 8/2002 | Hyde |
| 2002/0133153 A1 | 9/2002 | Hyde, Jr. |
| 2002/0138148 A1 | 9/2002 | Hyde, Jr. |
| 2002/0138149 A1 | 9/2002 | Hyde, Jr. |
| 2003/0097179 A1 | 5/2003 | Carter et al. |
| 2003/0163202 A1 | 8/2003 | Lakin |
| 2004/0092936 A1 | 5/2004 | Miller et al. |

FOREIGN PATENT DOCUMENTS

FR 2 684 543 6/1993

* cited by examiner

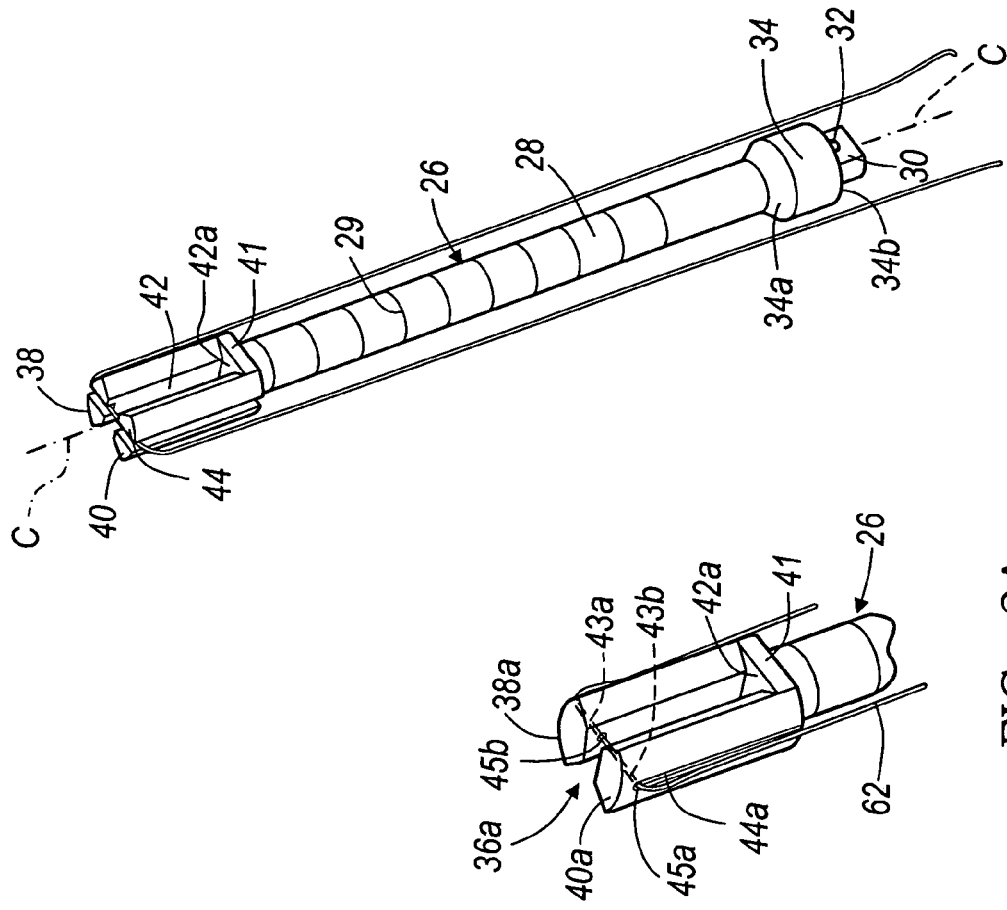
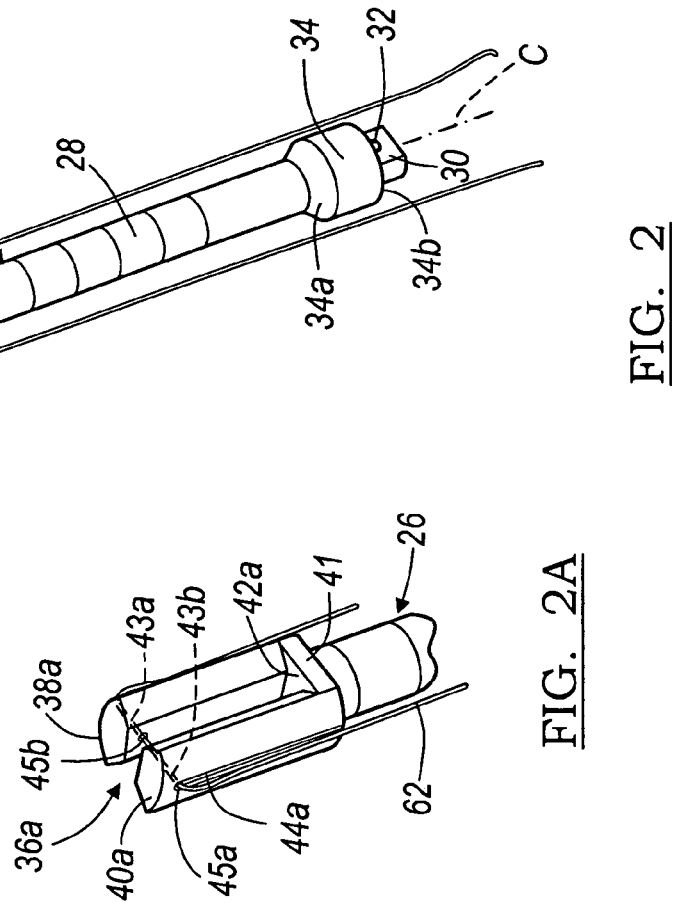
FIG. 2
FIG. 2A
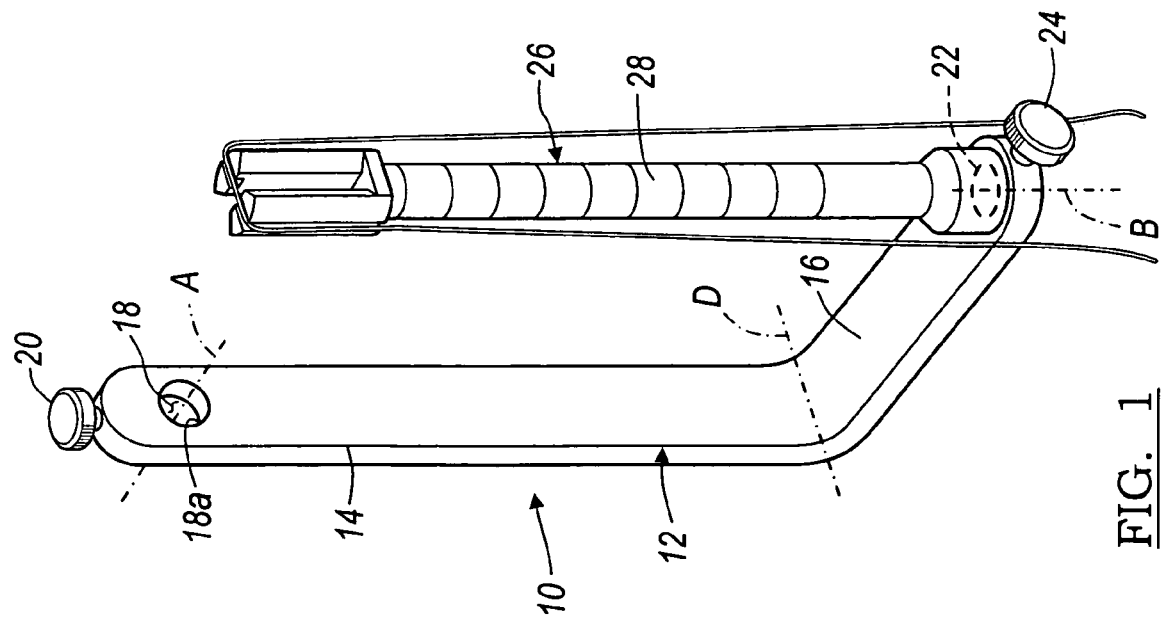
FIG. 1

APPARATUS AND METHOD FOR MANIPULATING A FLEXIBLE STRAND AND SOFT TISSUE REPLACEMENT DURING SURGERY

CROSS-REFERENCE TO RELATED APPLICATIONS

This application is a continuation-in-part of U.S. patent application Ser. No. 10/066,519 filed on Jan. 31, 2002. The disclosure of the above application is incorporated herein by reference.

FIELD

The present teachings relate to endoscopic soft tissue replacement fixation. More particularly, the present teachings relate to an apparatus and a method to reconstruct an anterior cruciate ligament with soft tissue replacements within a femoral tunnel.

BACKGROUND

The knee joint is frequently the object of injury and is often repaired using arthroscopic surgical procedures. An example of such arthroscopic surgical procedure is the replacement of anterior cruciate ligaments of the knee. The tearing of these ligaments is common in sports activities such as football or skiing.

Various natural and synthetic tissue replacements are used. The replacements can be xenograft, allograft or autograft. For example, fascia lata soft tissue replacements are flexible strands which are affixed to a threaded stud and turned into the femoral tunnel. Hamstring soft tissue replacements are also currently fixed over a screw in the tibial tunnel and fixed on the lateral femur. This technique requires the femoral tunnel to completely penetrate the femur. In addition, according to present procedures, fixation of the soft tissue replacement on the femoral side requires a large incision.

Further, various other graft portions, such as a patellar tendon graft, which can include a bone tendon bone graft can be used. The graft can be harvested from between patella and the selected bone to which the tendon is anchored. This allows for creation of a bone-tendon-bone graft where the tendon is already anchored to bone portions and only the bone portions are fixed relative to the implant site in the bone. Further examples include a quadriceps tendon graft as various examples of autografts. All grafts from similar sites of selected individuals can also be used in a patient requiring a graft. Further, xenograft materials can be harvested from compatible animals for implantation to selected patients. Also, synthetic materials, such as those that are biologically compatible and include appropriate physical properties can be used. One skilled in the art is generally aware of the various types of graft materials that can be provided for performing a grafting procedure.

It has been difficult to insert and fasten a soft tissue replacement in a blind hole or tunnel. Attempts have been made to thread the soft tissue replacement through the tunnel and over an anchor, but with some difficulty. Thus far, the prior art has not developed a quick and efficient way to implant a soft tissue replacement over an implanted anchoring system.

While offering certain improvements in arthroscopic surgery to repair ligaments, the prior art may still be improved upon to overcome the limitations on the endoscopic hamstring soft tissue replacement fixation due, in many instances, to the weakness of the flexible strand used to span the gap between the tendon soft tissue replacement and the fixation post.

Other techniques attempt to use biological fixation to augment or replace mechanical fixation. While increasing fixation strength these techniques require time to fully realize their fixation potential. Additionally the techniques may take additional surgical time and resources that a purely mechanical fixation technique may not require.

SUMMARY

An apparatus including a member that acts as a flexible strand insertion and guide rod is used to increase the simplicity and effectiveness of a soft tissue implant procedure. The member inserts a flexible strand, which has been preloaded onto the insertion rod, into a blind tunnel formed in a bone structure and provides a guide for a drill point or bit. Thus the member may be removed with the flexible strand already positioned in place to move an implant into the blind tunnel over the drill point. A cross or set pin can then be moved after the drill point into the drill hole to lock the implant in place.

The apparatus according to various embodiments allows a method of performing an implant procedure. A method of surgically implanting a soft tissue replacement for attaching two bone members comprises inserting an insertion rod having a flexible strand pre-loaded on the insertion rod into a first tunnel. A second tunnel can be formed transverse and through the first tunnel and the insertion rod with a tool bit. A flexible strand can be reached within the first tunnel. The method also includes removing the insertion rod from the first tunnel.

According to various embodiments an apparatus to assist in positioning a graft in a tunnel, having a diameter, formed in a bone while performing a surgery is disclosed. The apparatus can includes a guide member extending along a first axis and having a first end and second end. A guide portion can extend from the first end and generally along the first axis. An implant alignment member positionable relative to the guide portion can also be provided. Also, an engaging member can remove a portion of the alignment member from the tunnel. The alignment member is operable to align an implant and operable to hold the graft in the tunnel.

According to various embodiments a system for positioning a soft tissue graft in a bore formed in a bony portion of an anatomy is disclosed. The system can include a guide member positionable in a portion of the bore. An implant can hold the soft tissue graft in a portion of the bore. A positioning member can interconnect with the implant to align the implant with the bore. Also, an assisting member can interact with the positioning member to assist in positioning the positioning member relative to the soft tissue graft prior to positioning the implant.

According to various embodiments a method of surgically attaching a soft tissue graft to at least one bone member is disclosed. The method can include inserting an insertion rod having a guide portion into a first tunnel of the bone member. An engaging member can be positioned on the guide portion. A tunnel forming device can be positioned relative to the guide portion. A second tunnel can be formed transverse and through the first tunnel and relative to the guide portion. An implant aligning member can be passed through the second tunnel and through the guide section. An alignment suture member can be interconnected with the implant aligning member.

Further areas of applicability of the present teachings will become apparent from the detailed description provided hereinafter. It should be understood that the detailed description and specific examples, while indicating the various embodiments are intended for purposes of illustration only and are not intended to limit the scope of the teachings.

BRIEF DESCRIPTION OF THE DRAWINGS

The present teachings will become more fully understood from the detailed description and the accompanying drawings, wherein:

FIG. 1 is a perspective view of the bone insertion rod affixed to a U-Guide;

FIG. 2 is a perspective view of bone insertion rod not affixed to the U-Guide;

FIG. 2A is a detail perspective view of a guide portion of an insertion rod according to various embodiments;

DETAILED DESCRIPTION OF VARIOUS EMBODIMENTS

Figure 4:
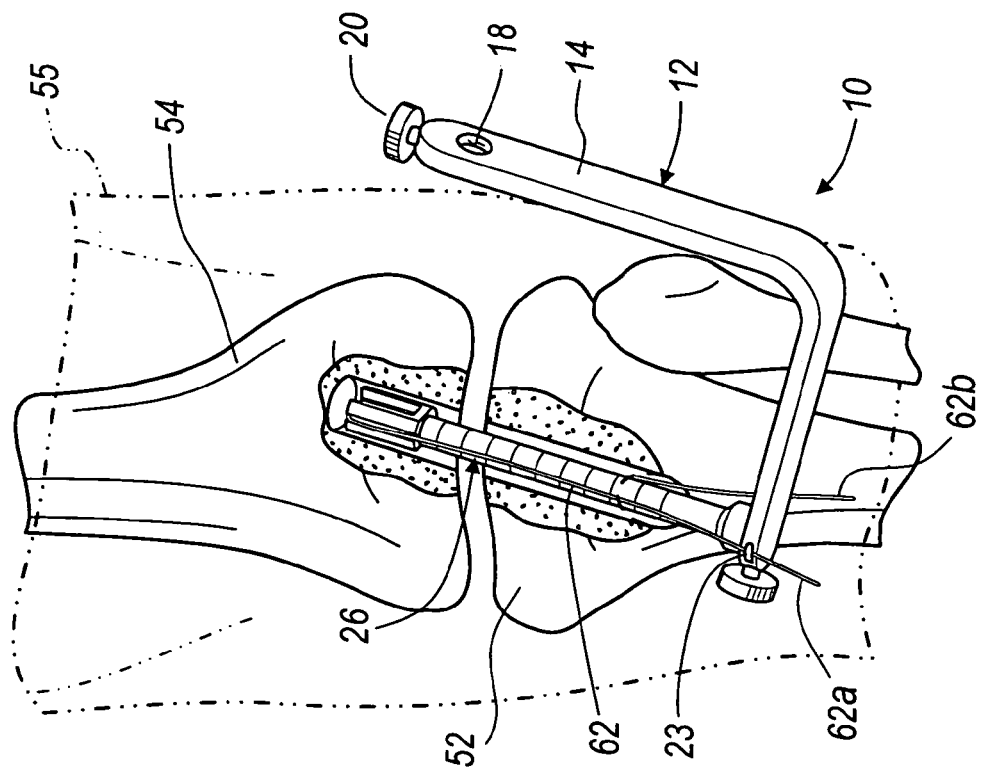
FIG. 4 is a perspective view of the insertion rod and U-Guide inserted into the tibia and femur tunnels with the flexible strand in place.

The following description of various embodiments is merely exemplary in nature and is in no way intended to limit the teachings, its application, or uses. Moreover, while the present teachings are directed in detail below with regard to ACL reconstruction, those skilled in the art will recognize the other types of soft tissue fixation may employ the present teachings.

Referring to FIG. 1, a generally guide apparatus 10 which may be generally a U-shaped guide or a U-Guide generally includes an L-shaped retaining bar or L-guide 12 which includes two portions or legs, a first portion 14 and a second portion 16, that is substantially perpendicular to the first portion 14. The first portion 14 defines a guide section 18, having a guide section ledge 18a, formed transversely through the first portion 14. The guide section may be a passage through or transverse to the first portion 14 such as a bore wherein the guide section ledge would be a bore ledge. A set screw 20 can be provided to create a locking mechanism for the guide section 18. The second portion 16 defines a bore 22 formed transversely through the second portion 16. Also, a flexible strand notch or flexible strand retaining member 23 is formed near the bore 22 on the second portion 16. A second set screw 24 is also provided to create a locking mechanism for the bore 22. The L-guide 12 is shown in an L-shape, however, it will be understood the L-guide 12 may be any appropriate form. Generally, however, the axes defining the guide section 18 and the bore 22 are orthogonal. Therefore, the first axis A of the guide section 18 should intersect the second axis B of the bore 22 at a right angle at a position.

An insertion or guide rod 26 is adjustably held in the bore 22 and locked in place with the second set screw 24. With continuing reference to FIG. 1 and further reference to FIG. 2, the insertion rod 26 includes a body portion 28. The body portion 28 is substantially cylindrical and formed around a longitudinal axis C. The body portion 28, which is generally a solid, may also taper towards the guide portion 36 (described herein). Also, the body portion 28 may include depth indicia 29 to give a visual indication of the depth of the insertion rod 26 into a patient.

Extending from a first end of the body portion 28 is an L-Guide engaging portion 30 which includes a notch or projection 32 that is received in the second portion 16 of the L-Guide 12 to ensure proper orientation of the insertion rod 26 to the L-Guide 12. The notch 32 on the insertion rod 26 is keyed to be received on to a portion of the second portion 16. The insertion rod 26 further includes a collar 34, having a first shoulder 34a and a second shoulder 34b, to ensure that the insertion rod 26 is held at a predetermined depth in the L-Guide 12 and to further ensure proper orientation of the insertion rod 26 relative to the L-Guide 12.

A guide portion 36 extends from a second end of the body portion 28. The guide portion 36 includes two generally parallel legs 38 and 40 and a shoulder 41. Each leg 38, 40 extends from the body portion 28 along axis C, though offset therefrom. The two legs 38, 40 define a slot 42, where the slot 42 extends substantially the distance of the two legs 38, 40 and has a slot ledge 42a where the two legs 38, 40 meet at the shoulder 41.

Also formed in each of the legs 38, 40 is a flexible strand groove 44. The flexible strand groove 44 may be any appropriate depth, but exemplary is substantially equal in depth to the diameter of a cord or flexible strand thread to be used with the apparatus 10. The flexible strand groove 44 extends, along the outside of each leg 38, 40, substantially the length of the legs 38, 40 and also over the distal end of the legs 38, 40. The flexible strand groove 44 also extends generally along axis C, though offset therefrom, and also over the terminal end of each leg 38, 40. The plane defined by the slot 42 is substantially orthogonal to the plane defined by the flexible strand groove may lie on any relative plane as long as the two planes intersect within the area defined by the guide portion 36. As described herein, a tool may be placed through the slot 42 while a cord is placed over the slot 42 by being positioned in the flexible strand groove 44.

The insertion rod 26 may be any desired length. Preferably, however, the distance between the second collar shoulder 34b and the slot ledge 42a is equal to the distance between a first end of the first portion 14, generally represented by line D, and the guide section ledge 18a. In this way, the guide section ledge 18a and the slot ledge 42a are generally equidistant from the second portion 16. Therefore, any instrument received through the guide section 18 would remain substantially parallel to the second portion 16 when it passed through the slot 42.

The flexible strand groove 44 can be placed orthogonally to the slot 42 so that a cord, such as a flexible strand, may be placed in the flexible strand groove 44 to form an enclosed passage for any device that may be placed through the slot 42. In this way, a device, such as a K-Wire (described herein), when inserted through the slot 42a has a flexible strand looped over the device. It will be understood, however, that the flexible strand groove 44 may be formed at any orientation relative to the slot 42 as long as a flexible strand placed in the flexible strand groove 44 will overlay the slot 42.

The notch 32 ensures that the insertion rod 26 is properly oriented with the L-Guide member 12 of the U-guide apparatus 10. In particular, the slot 42 is preferably aligned with the guide section 18. The set screw 24 tightens against the L-Guide engaging portion 30 to ensure that the insertion rod 26 does not move during a surgical procedure. Also, this ensures the proper keyed fit of the notch 32 into the second portion 16 so that the guide section 18 and the slot 42 are properly aligned. This ensures that the instrument received through the apparatus 10 is aligned. It will be understood, however, that any appropriate means may be used to secure the insertion rod 26 to the L-Guide member 12 of the apparatus 10.

Returning briefly to FIG. 2A, the insertion or guide rod 26 can include a guide portion 36a. The guide portion 36a can be similar to the guide portion 36. For example, the guide portion 36a can include a first leg 38a and a second leg 40a and a slot 44a similar to the slot 44. The guide portion 36a can also include a bore 45a that extends as a passage 43a through the leg 40a. The guide portion 36a can further include a second bore 45b that extends as a passage 43b through the leg 38a. Therefore, rather than the flexible strand 62 being placed in the slot 44, the flexible strand 62 can pass through the passages 43a, 43b and through the bores 45a, 45b to be securely held relative to the guide portion 36a. The slot 44a could be provided to allow movement of the guide portion 36a through a tunnel without impinging the flexible strand 62. It will be understood that the guide portion 36a can be formed in any appropriate manner, such as the guide portion 36a, the guide portion 36, or any appropriate guide portion. The inclusion of the passages 43a, 43b, however, can assist in holding the flexible strand 62 at a selected position relative to the guide portion 36a d using insertion of the member 26.

Referring to the remaining FIGS. 3-9, an exemplary method for using the apparatus 10, including the insertion rod 26 is described. It will be understood that although the apparatus 10 is described in the use of an Anterior Cruciate Ligament (ACL) replacement, any appropriate surgery may be performed with the apparatus 10 which would require its attributes.

Figure 3:
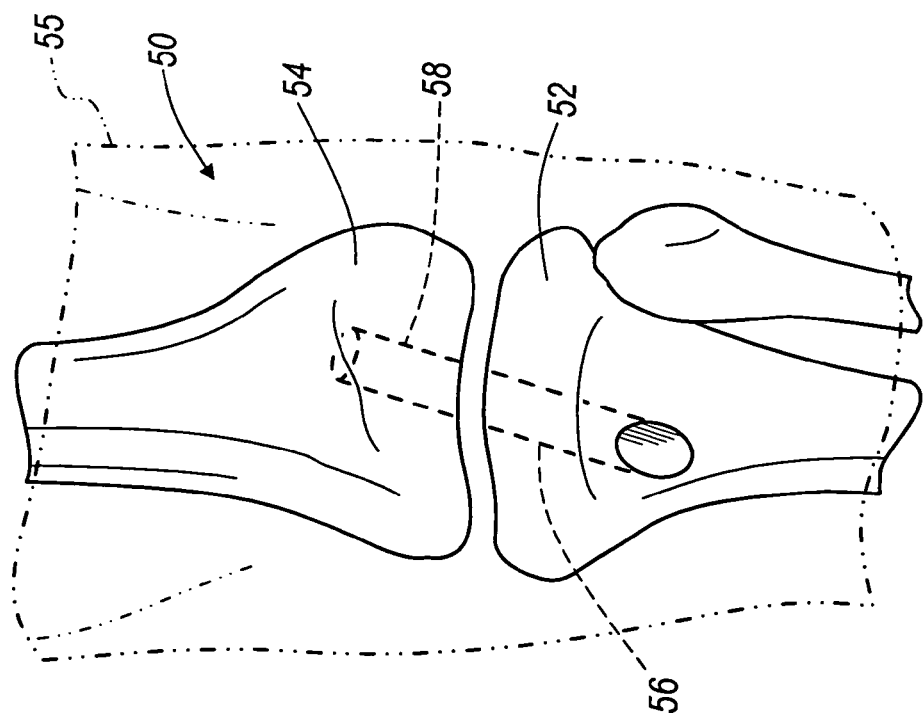
FIG. 3 is an exemplary view of a knee prepared for insertion of the insertion rod.

With particular reference to FIG. 3, a knee 50 generally includes at least a tibia 52 and a femur 54 surrounded by soft tissue 55. The knee 50 is initially prepared by forming a tibial tunnel 56 and a femoral tunnel 58 which are substantially in line with one another such that a straight and solid object could engage both the tibial tunnel 56 and the femoral tunnel 58 without a substantial amount of stress when the knee is placed in flexion between about 30 degrees and 110 degrees. It is understood that incisions must first be made in the soft tissue 55 surrounding the tibia 52 such that a tool may engage the tibia 52 and the femur 54 to form the tibial tunnel 56 and the femoral tunnel 58. Any suitable tool may produce the respective tunnels 56, 58 such as a pneumatic or electric drill or reamer. It is also understood that the femoral tunnel 58 is a blind tunnel. A blind tunnel is a tunnel which includes an entrance but no discernable exit, rather a blind tunnel terminates below the surface of the femur 54.

The size of the tibial tunnel 56 and the femoral tunnel 58 depends upon the size of the soft tissue replacement (described further herein) to be implanted into the patient. The larger the replacement needed, the larger the diameter of the tibial tunnel 56 and the femoral tunnel 58. The tibial tunnel 56 and femoral tunnel 58 may be of any required diameter, but are generally between about 5 and 18 millimeters. It would be understood, however, that if a larger diameter replacement is necessary, then larger diameter tunnels 56, 58 may be produced in the tibia 52 and femur 54 to receive the implant. Additionally, smaller tunnels 56, 58 may be used if only a smaller implant is necessary. In addition, the largest area of the insertion rod 26 will have a diameter substantially equal to the diameter of the tibial tunnel 56 and femoral tunnel 58. For example, if the insertion rod 26 was produced so that the guide portion 36, in particular the shoulder 41, form the largest diameter of the insertion rod 26, then the outside diameter of the guide portion 36 would be substantially equal to diameter of the tibial tunnel 56 and the femoral tunnel 58. Also, the body portion 28 may have a lesser diameter, or a taper towards the shoulder 41, to ease insertion and removal of the insertion rod 26. This ensures that the insertion rod 26, and particularly the slot 42, are substantially centered in the femoral tunnel 58 for the remaining procedure.

A flexible strand 62, having a trailing end 62a and a leading end 62b, is placed or pre-loaded into the flexible strand groove 44 and then the insertion rod 26 is inserted through the tibial tunnel 56 and into the femoral tunnel 58, as best shown in FIG. 4 (see also FIGS. 1 and 2). The flexible strand 62 may be any generally known strand suitable to the purpose such as a mono- or poly-filament suture, a flexible wire, or cord made of any suitable material. The flexible strand groove 44 allows the flexible strand 62 to be inserted through the tunnels 56, 58 without engaging the walls of the tunnels 56, 58. Generally the depth of the flexible strand groove 44 is at least equal to the diameter of the flexible strand 62. The flexible strand 62 is placed so that it reaches substantially to the end of the femoral tunnel 58 and the slot 42 creates an opening through the center of the femoral tunnel 58 through which an instrument may pass, while not interrupting the flexible strand 62 which has been inserted into the femoral tunnel 58 by the insertion rod 26. The flexible strand 62 is caught in the flexible strand notch 23. The flexible strand 62 is held in position during the insertion of the insertion rod 26 into the tunnels 56, 58 and during the remaining surgical procedure by the flexible strand notch 23. Any suitable means may be used to hold the flexible strand 62 in place relative to the L-Guide member 12 of the apparatus 10. The flexible strand notch 23, which holds the flexible strand 62 with friction, is merely exemplary of one appropriate means to hold the flexible strand 62 in place.

Once the insertion rod 26 has been inserted into the femoral tunnel 58, so that the flexible strand 62 is positioned properly, a device, such as a drill bit or point 70 is used to produce a transverse tunnel 72 in the femur 54. The transverse tunnel 72 is formed transversely to the femoral tunnel 58. The transverse tunnel 72 will include an insertion point 72a and an exit point 72b. It will be understood that an incision must first be made in the soft tissue 55 surrounding the femur 54, so that the drill bit or point 70 may engage the femur 54 to form the transverse tunnel 72. The drill point 70 may be powered by any appropriate device known in the art such as an electric or pneumatic drill. Furthermore, additional guide units or bullets 74, such as the U-Guide bullet produced by Arthotek, Inc. of Warsaw, Ind., may be used to ensure the proper orientation and depth of the drill point 70. The guide bullet 74 is inserted into the guide section 18 and held in place with the set screw 20 to ensure the drill point 70 is properly aligned with the slot 42 when producing the transverse tunnel 72. The transverse tunnel 72 is produced through the entire width of the femur 54 so that the drill point 70 exits the femur 54 producing the exit point 72b. This allows the drill point 70 to be removed through the exit point 72b at the appropriate time. While the apparatus 10 is still in place, a cannulated reamer (not shown) enlarges a portion of the transverse tunnel 72. The reamed tunnel 73 receives the pin 84 (described herein). The reamed tunnel 73 does not extend the length of the transverse tunnel 72.

Figure 6:
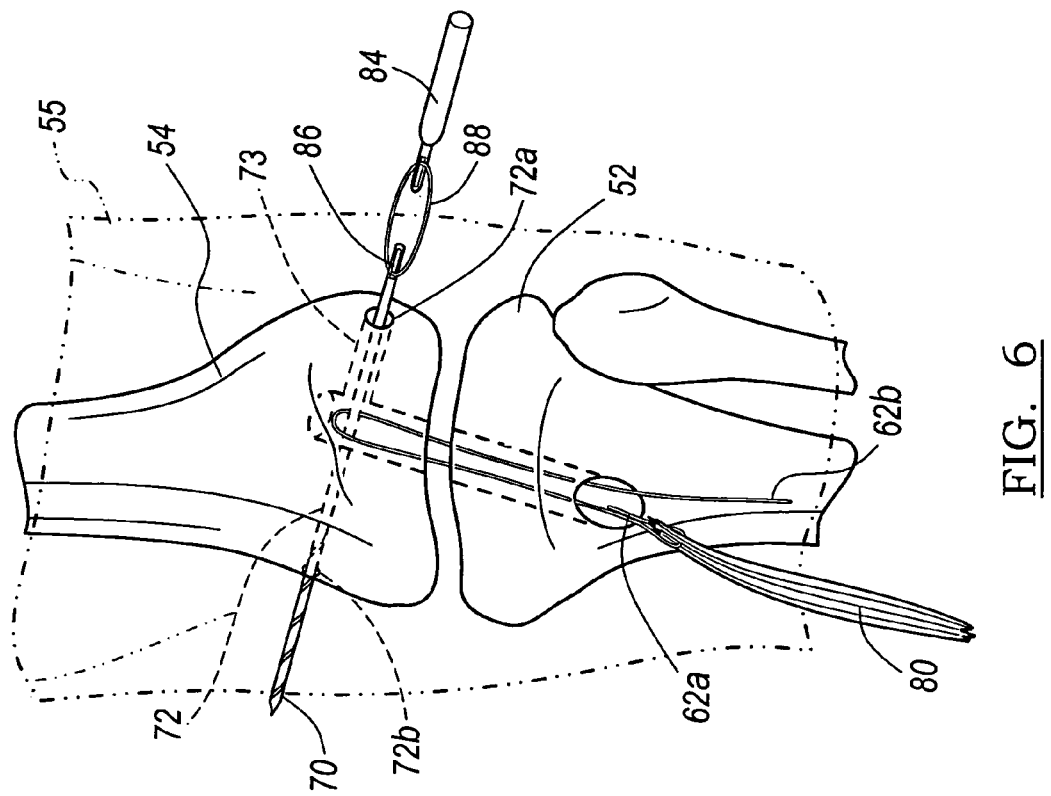
FIG. 6 is perspective view of the K-Wire Drill Point with the flexible strand affixed to a soft tissue replacement and draped over the K-Wire Drill Point.
Figure 5:
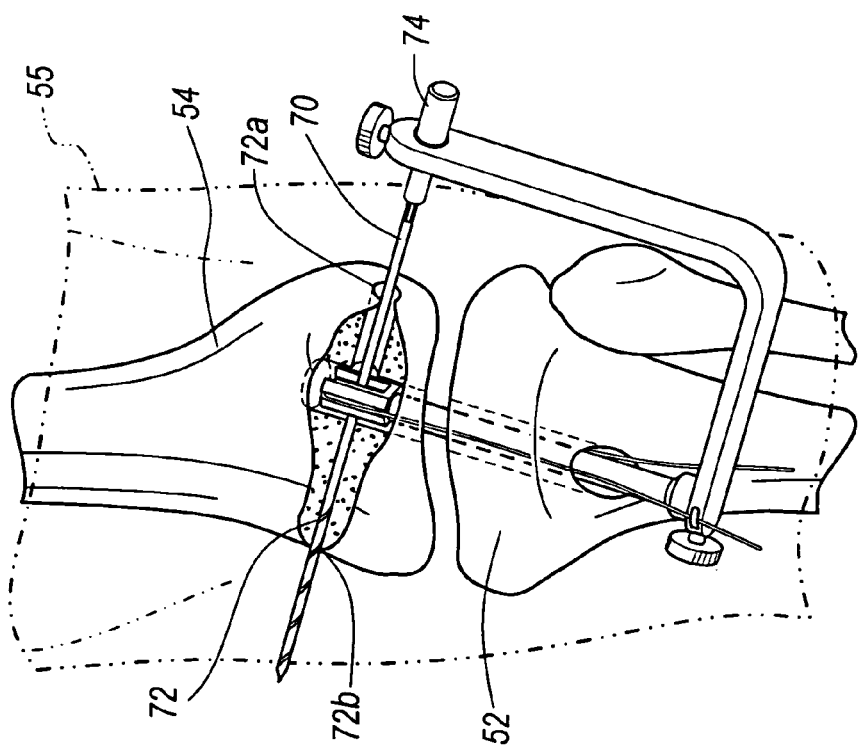
FIG. 5 is a view of the U-Guide and insertion rod in place with a K-Wire Drill Point forming a transverse tunnel.
Figure 7:
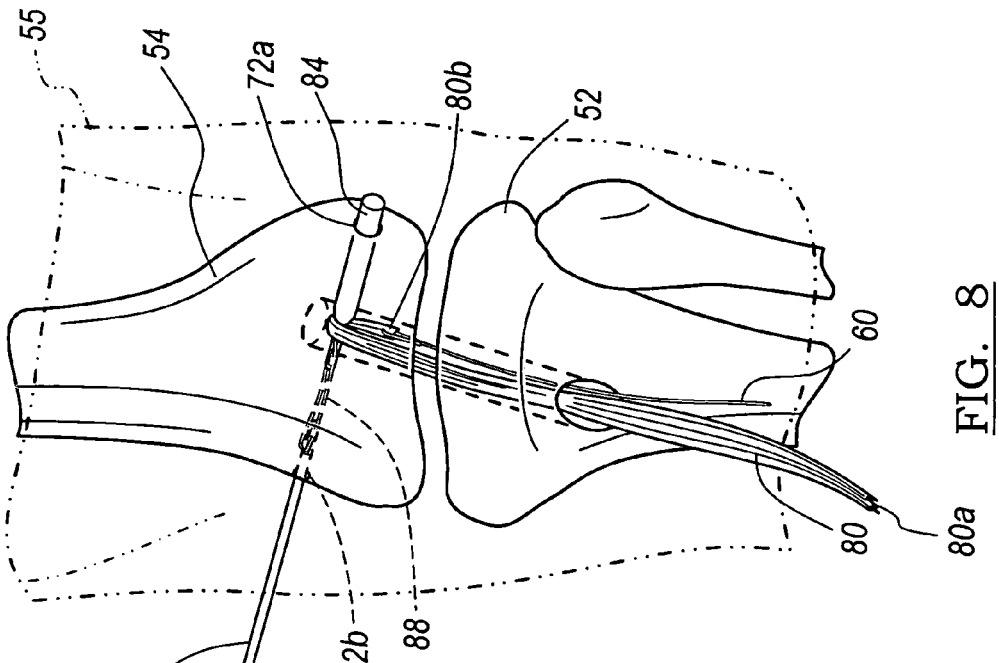
FIG. 7 is a perspective view of the soft tissue replacement pulled over the K-Wire and out through the tibial tunnel.
Figure 8:
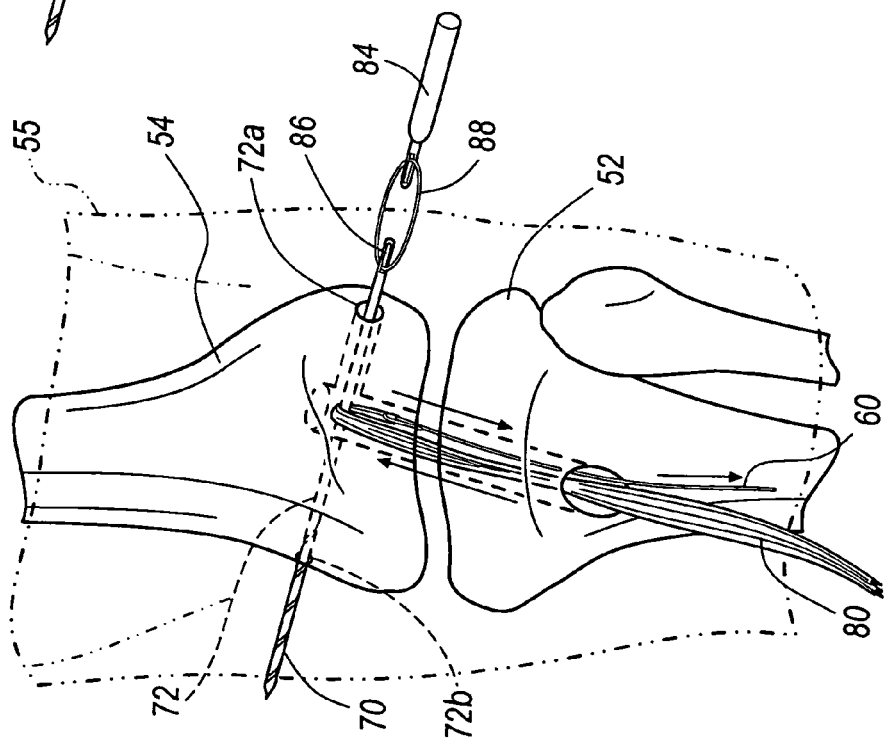
FIG. 8 is a perspective view of the soft tissue replacement in place and the ACL Cross Pin set in place in the transverse tunnel in the femur.

After the reamed tunnel 73 is produced, the apparatus 10, is removed as particularly shown in FIG. 6. Once the apparatus 10 has been removed, the drill point 70 remains in the transverse tunnel 72. A soft tissue replacement 80 is affixed to the trailing end 62a of the flexible strand 62. The soft tissue replacement may be any suitable replacement such as a hamstring portion, an allograft tissue replacement, a xenograft tissue replacement, or an artificial soft tissue replacement which may be produced from materials such as polymers or metal. After the soft tissue replacement 80 has been affixed to the trailing end 62a, the leading end 62b of the flexible strand 62 is pulled drawing the soft tissue replacement 80 first through the tibial tunnel 56 and then through the femoral tunnel 58 over the drill point 70 and back down the femoral tunnel 58 and out through the tibial tunnel 56. This produces a loop of the soft tissue replacement 80 over the drill point 70 inside of the femoral tunnel 58. After being looped over the drill point 70, the two free ends 80a and 80b of the soft tissue replacement 80 extend from the tibial tunnel 56 adjacent to the tibia 52.

After the soft tissue replacement 80 has been looped over the drill point 70, an ACL cross pin or pin 84 is pulled into place in the reamed tunnel 73. The drill point 70 generally includes an eyelet 86 which will allow the attachment of the pin 84 to the drill point 70. Generally, the pin 84 is attached to the eyelet 86 through a second flexible strand 88 or other appropriate means. After the pin 84 is attached to the eyelet 86, the drill point 70 is pulled through the transverse tunnel 72, through the loop of the soft tissue replacement 80 and out the exit point 72b. This pulls the pin 84 into position and fixes it within the transverse tunnel 72, as particularly shown in FIG. 8. Once the pin 84 has been fixed in place in the transverse tunnel 72, the attached flexible strand 88 may be cut or otherwise disengaged from between the eyelet 86 and the pin 84. The drill point 70 is then freely removed from the transverse tunnel 72. This leaves the pin 84 lodged into the transverse tunnel 72 which may be locked in place with either portions of the pin 84 or through any other appropriate locking means. Although any appropriate means may be used to hold pin 84 in the reamed tunnel 73, the pin 84 may include a square end to hold pin 84 in place. The pin 84 may also be threaded such as the device described in U.S. Pat. No. 5,674,224 entitled "Bone Mulch Screw Assembly For Industrial Fixation of Soft Tissue Soft tissue replacements And Method For Using Same" to Stephen M. Howell et al. incorporated herein by reference.

Figure 9:
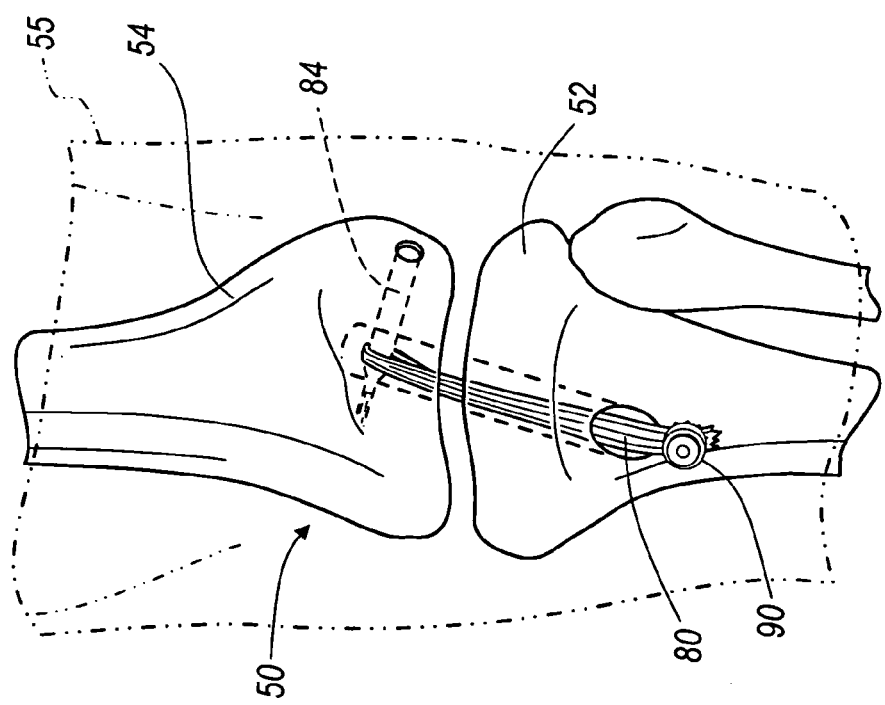
FIG. 9 is a deep view of the knee with an ACL replacement having its free ends affixed to the tibia and the femoral end affixed over the ACL Cross Pin.

Because the pin 84 has been lodged in the transverse tunnel 72, and the soft tissue replacement 80 is looped over the pin 84, only the free ends 80a and 80b need to be secured to the tibia 52 to complete the implantation. A staple 90 is used to affix the free ends 80a and 80b of the soft tissue replacement 80 to the tibia 52, as best shown in FIG. 9. It will be understood, however, that any appropriate means may be used to affix the free ends 80a, 80b to the tibia 52 such as The Washer-Loc™ tibial fixation device sold by Arthrotek, Inc., of Indiana, U.S.A.; U.S. Pat. No. 6,280,472 B1 entitled "Apparatus And Method For Tibial Fixation Of Soft Tissue" to James A. Boucher et al.; and U.S. Pat. No. 5,931,869 entitled "Apparatus And Method For Tibial Fixation Of Soft Tissue" to James A. Boucher et al. each incorporated herein by reference. Once the free ends 80a and 80b of the soft tissue replacement 80 are affixed to the tibia 52, the soft tissue replacement 80 securely attaches the tibia 52 and the femur 54 substantially as a natural ACL would.

It will be understood that any appropriate means may be used to affix the soft tissue replacement 80 in the femoral tunnel 58. The pin 84 is merely exemplary of any appropriate device to affix the soft tissue replacement 80 in the femoral tunnel 58. Any commonly known screw or other fixation device may be used to fix the soft tissue replacement 80 in the femoral tunnel 58. It will also be understood that the soft tissue replacement 80 may be pulled over the pin 84 after the pin 84 has been lodged in the transverse tunnel 72. In particular, if the pin 84 is smooth, the soft tissue replacement 80 may be pulled over the pin 84 without damaging the soft tissue replacement 80 itself. The drill point 70 is simply removed from the transverse tunnel 72 before the soft tissue replacement 80 is pulled into the femoral tunnel 58.

It will also be understood that the method for performing the described procedure may be altered but remain within the scope of the presently claimed invention. For example the flexible strand 62 may looped over the insertion rod 26 such that the two free ends 62a and 62b are on one side and a loop of the flexible strand is formed on the other side of the insertion rod 26. Thus the soft tissue replacement 80 may be affixed to both free ends 62a and 62b or placed through the loop and then pulled over the insertion rod 26.

As discussed above, the guide apparatus 10 includes a plurality of components including the L-guide portion 12, which includes a guide section 18 defining a guide ledge 18a. The insertion or guide rod 26 can be interconnected with the L-guide 12 to form a portion of the guide apparatus 10. Although the guide apparatus 10 can be used according to various embodiments, including that described above, various other methods and procedures can be performed with the similar apparatus.

It will be understood that the guide apparatus 10 can be used to perform a plurality of procedures, such as assisting in replacing an anterior cruciate ligament (ACL) in a knee joint between the femur 54 and the tibia 52. It will be understood that various procedures can be performed, such as with initial reference to FIGS. 3-5. As described and illustrated above and briefly summarized below, a soft tissue replacement can be performed relative to the knee 50. The tibial tunnel 56 and the femoral tunnel 58 can be formed in the tibia and the femur 54, respectively. It will be understood that various and appropriately sized incisions can be made in the soft tissue 55 as necessary and any appropriate apparatus can be used to form the tunnels 56, 58.

Figure 10:
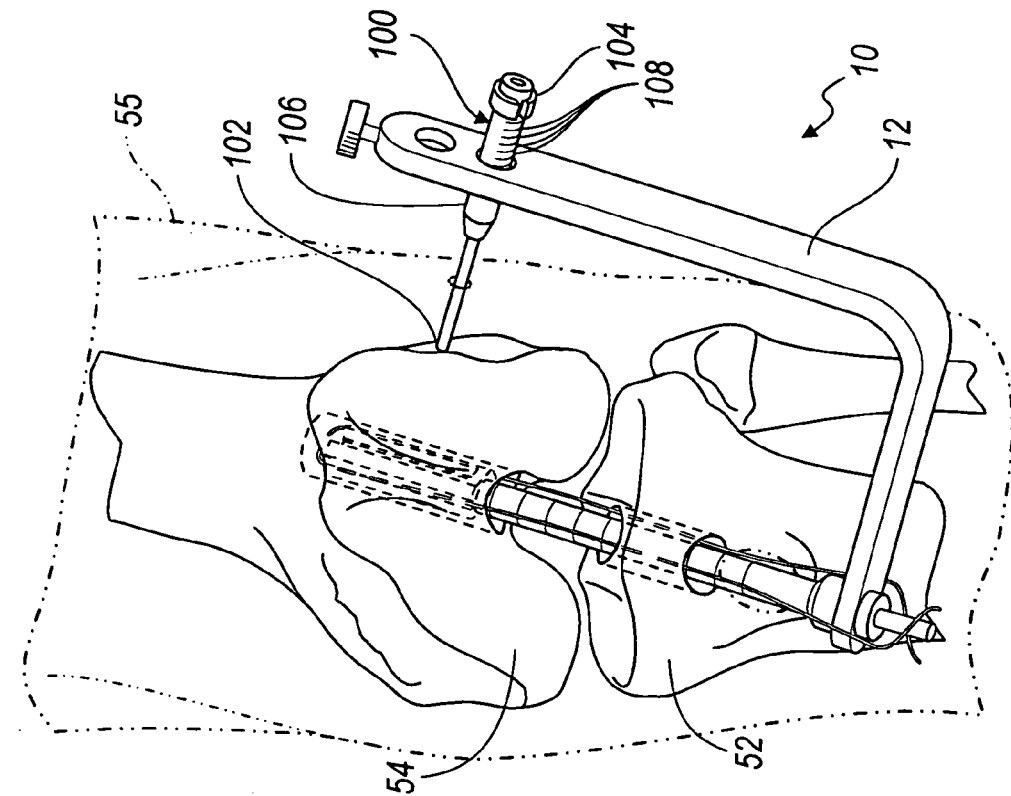
FIG. 10 is an environmental perspective view of an apparatus according to various embodiments positioned relative to a knee with a measuring device.

With reference to FIG. 10, the guide apparatus 10 can be positioned relative to the knee 50. In particular, the guide rod 26 can be positioned in the tunnels 56, 58. The guide rod 26 can be positioned in the tunnels 56, 58 either prior to or after being interconnected with the L-guide portion 12. Further, as discussed above, the guide rod 26 can include an engaging member, such as a pre-loaded flexible strand 62. Once the guide apparatus 10 is positioned relative to the tibia 52 and the femur 54 through the tunnels 56, 58, a targeting bullet or sizing member 100 can be passed through the guide section 18. The sizing member 100 can be passed through an incision made in the soft tissue 55 as will be understood by one skilled in the art.

The sizing member 100 which can be similar to or the same as the bullet 24, can include a distal or bone engaging end 102 and a proximal end 104 interconnected by a body 106. The body 106 can include one or a plurality of demarcations 108 that can be referenced relative to the L-guide portion 12. The sizing member 100 can be used to select an appropriate implant, such as the graft fixation pin 84. The graft fixation pin 84 can be selected based on various characteristics, such as the depth to the soft tissue 55, the size of the femur 54 relative to the soft tissue 55, the depth of the femur 54, the positioning of the tunnel 58 within the femur 54, or any other appropriate consideration. Regardless, the sizing member 100 may be used during the procedure to assist in selecting an appropriate graft fixation pin 84. It will be understood, however, that the sizing member 100 is not necessary and any appropriate method can be used to select the graft fixation pin 84.

Figure 11:
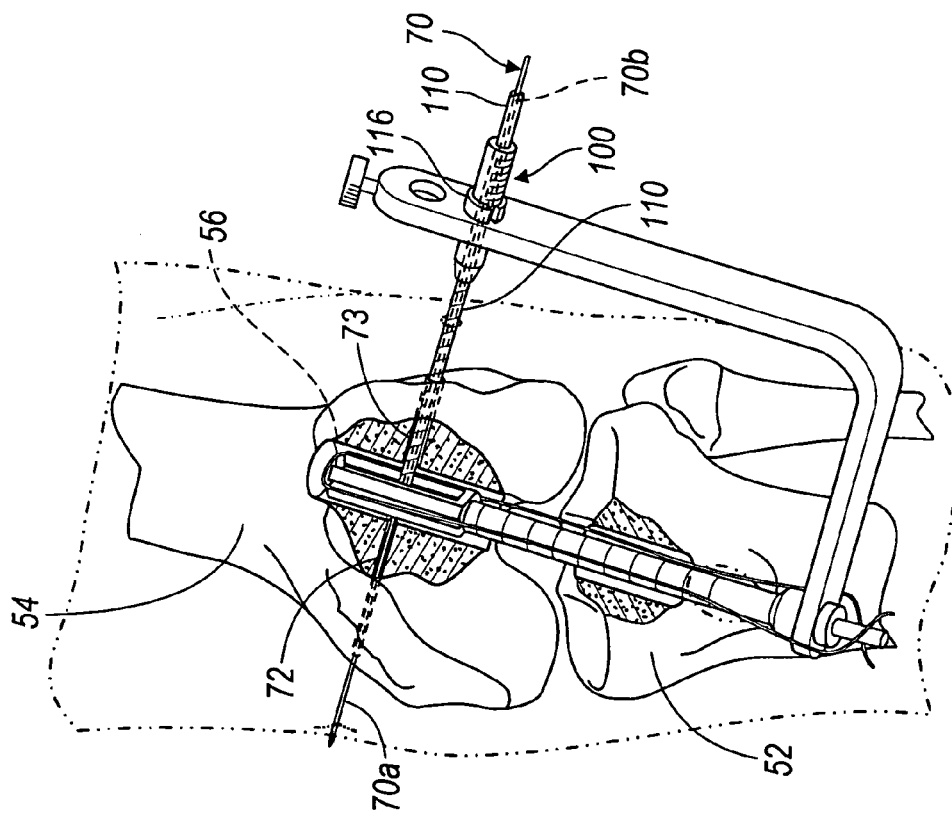
FIG. 11 is an environmental perspective view of an apparatus according to various embodiments positioned relative to a knee with a drill point through the femur.

After positioning the sizing member 100 relative to the guiding apparatus 10 and the femur 54, the guide wire or drill point 70 can be positioned through the sizing member 100 and drilled through the femur 54 as illustrated in FIG. 11. This can be used to form a portion of the transverse tunnel 72 through the femur 54. As discussed above, the drill point 72 can pass through the guide portion or the opening 42 in the guide rod 26. The drill point 70 can be passed through the entire length or width of the femur 54. The drill point 70 may extend out a side of the femur 54 so that a distal tip 70a of the drill point extends out of the femur along with a proximal end 70b of the drill point 70. This may allow for either end of the drill point 70 to be operated for various purposes, such as those described herein. It will be understood, however, that the drill point 70 can be passed through the femur 54 in any appropriate manner with the use of the guide apparatus 10, without the use of the guide apparatus 10, or with or without the sizing member 100. The drill point 70 can be powered by hand or with a power tool, or in any appropriate manner. It will be understood that the guiding apparatus, if used, can include portions that allow the drill guide 70 to be positioned relative to the femur 54 in any appropriate manner.

Once the drill point 70 is passed through the femur 54, such as by drilling the drill point 70 through the femur, a portion of the transverse tunnel 72 can be enlarged. A drill bit 110 can be used to form the enlarged portion 73 of the transverse tunnel 72. The drill bit 110 can also be powered in any appropriate manner such as with a power drill motor, a hand tool, or the like. Further, the drill bit 110 can be any appropriate member that is able to perform the enlargement of transverse tunnel 73. For example, a reamer, a cannulated drill bit, or any other appropriate tool can be used to form the enlarged transverse tunnel 73.

The drill bit 110 can be drilled over the drill point 70 to any appropriate depth in the femur 54. For example, the drill bit 110 can be drilled into the femur 54 until it reaches or bottoms out on the guide rod 26. Therefore, when the drill bit 110 reaches the guide rod 26, it will be understood that the drill bit 110 has formed the enlarged tunnel 73 from an exterior of the femur 54 to at least a portion of the femoral tunnel 56. The enlarged and tunnel portion 73 can be used for any appropriate portion, such as positioning the cross pin or bullet 84 into the femur 54.

Figure 12:
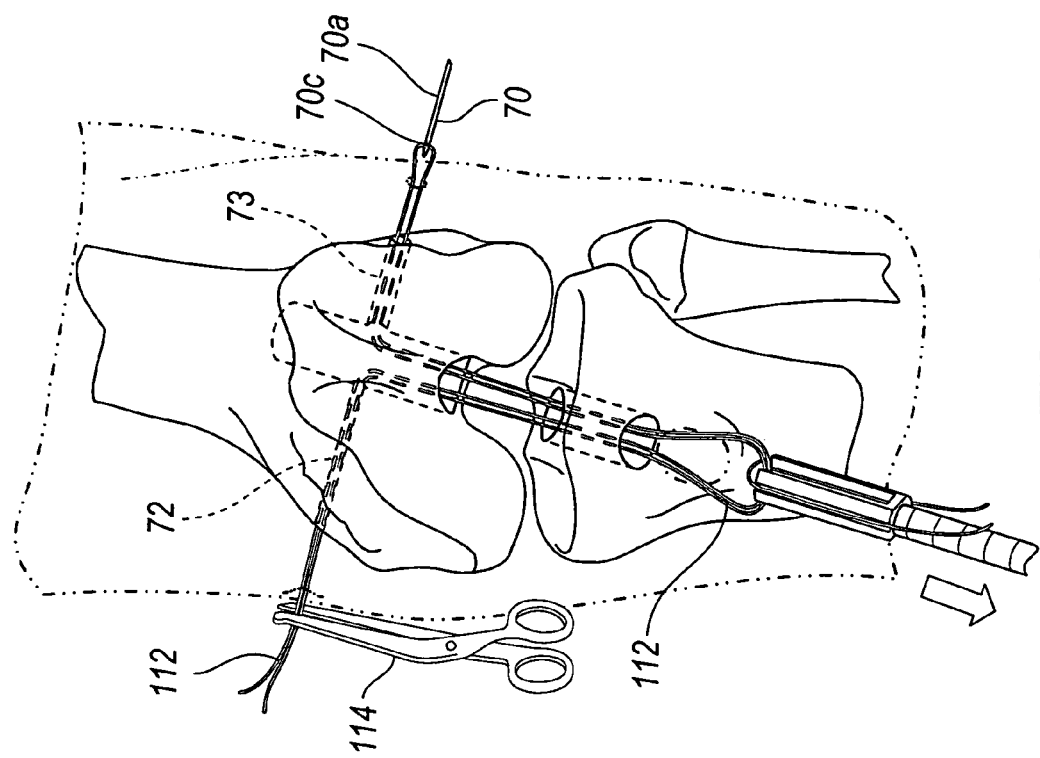
FIG. 12 is an environmental perspective view of an apparatus according to various embodiments positioned relative to a knee with a pin alignment suture through the femur.

Once the enlarged portion 73 of the transverse tunnel is formed, a transverse pin alignment suture or flexible member 112 can be interconnected with an eyelet 70c formed on the drill point 70, as illustrated in FIG. 12. The transverse pin alignment suture 112 can then be drawn through the transverse tunnel 72 by withdrawing the drill point 70 therefrom. An external portion of the suture 112 can be clamped or held in place with any appropriate mechanism such as with a clamp 114.

Figure 13:
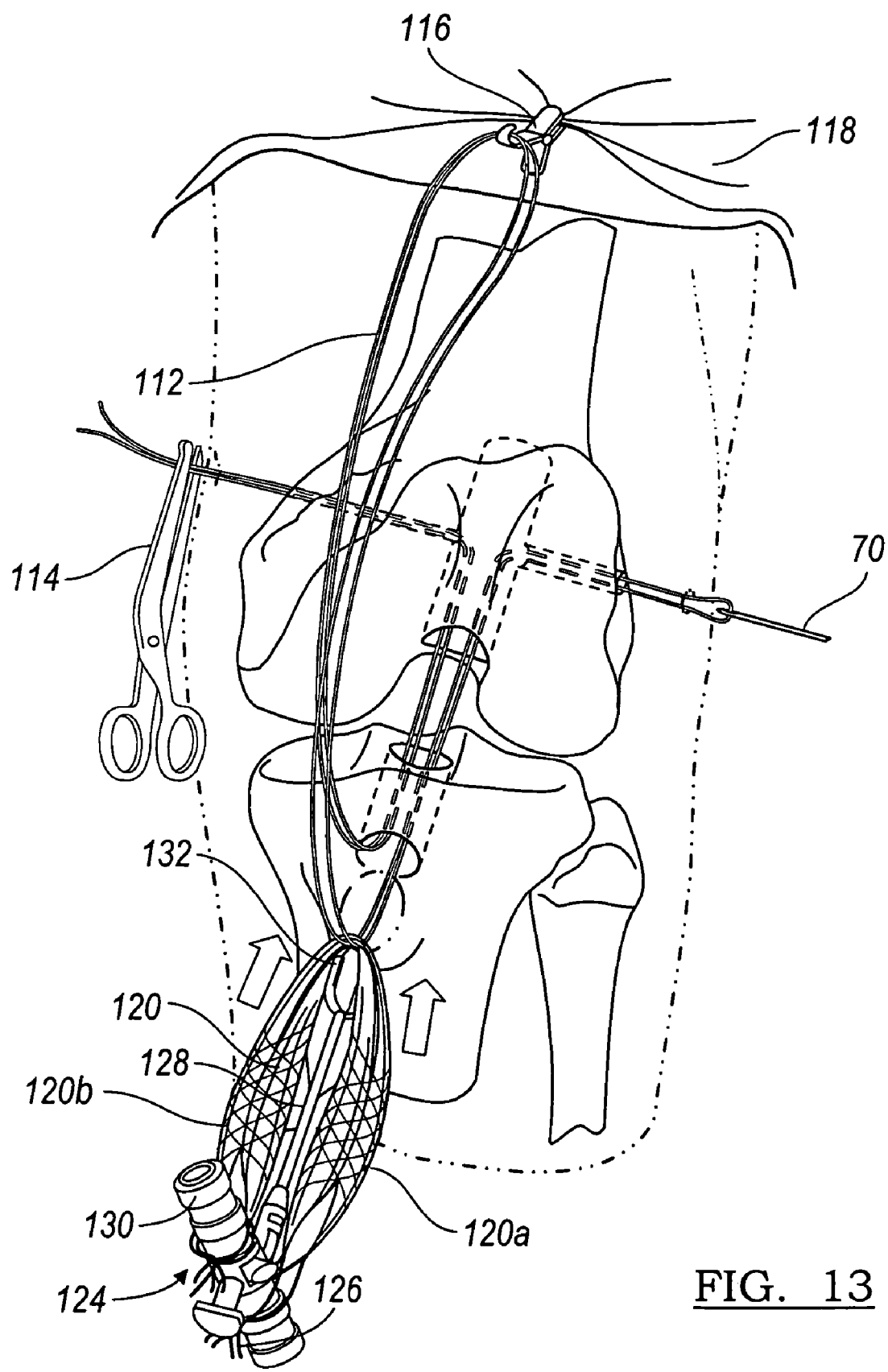
FIG. 13 is an environmental perspective view of an apparatus according to various embodiments positioned relative to a knee with a pin alignment suture through the femur and a graft pusher in a first position relative to the femur.

Once the pin alignment suture 112 is drawn through the transverse tunnel 72, the guide apparatus 10 can be substantially removed from the knee 50. The flexible member 60 that is initially loaded on the guide rod 26 can be used to withdraw a portion of the pin alignment suture 112 out of the tibial tunnel 56. The portion of the suture 112 drawn out of the tibula tunnel 56 can be clipped to any appropriate portion or held in a relative location such as being clipped with a clip 116 to a drape 118, as illustrated in FIG. 13. It will be understood, however, that the pin alignment suture 112 can be held in any appropriate manner exterior to the tibia 52. Although it has been disclosed above that the flexible member can be used to withdraw a portion of the pin alignment suture 112 from the tibial tunnel 56, it will be understood that any appropriate enlargement mechanism can be provided. For example, a releasable member, such as a finger or a clip, can be formed on the guide rod 26 that can be used to withdraw the pin alignment suture 112. Therefore, it will be understood, that the flexible member 60 is merely exemplary of a mechanism or instrument to withdraw a portion of the pin alignment suture 112.

Figure 14:
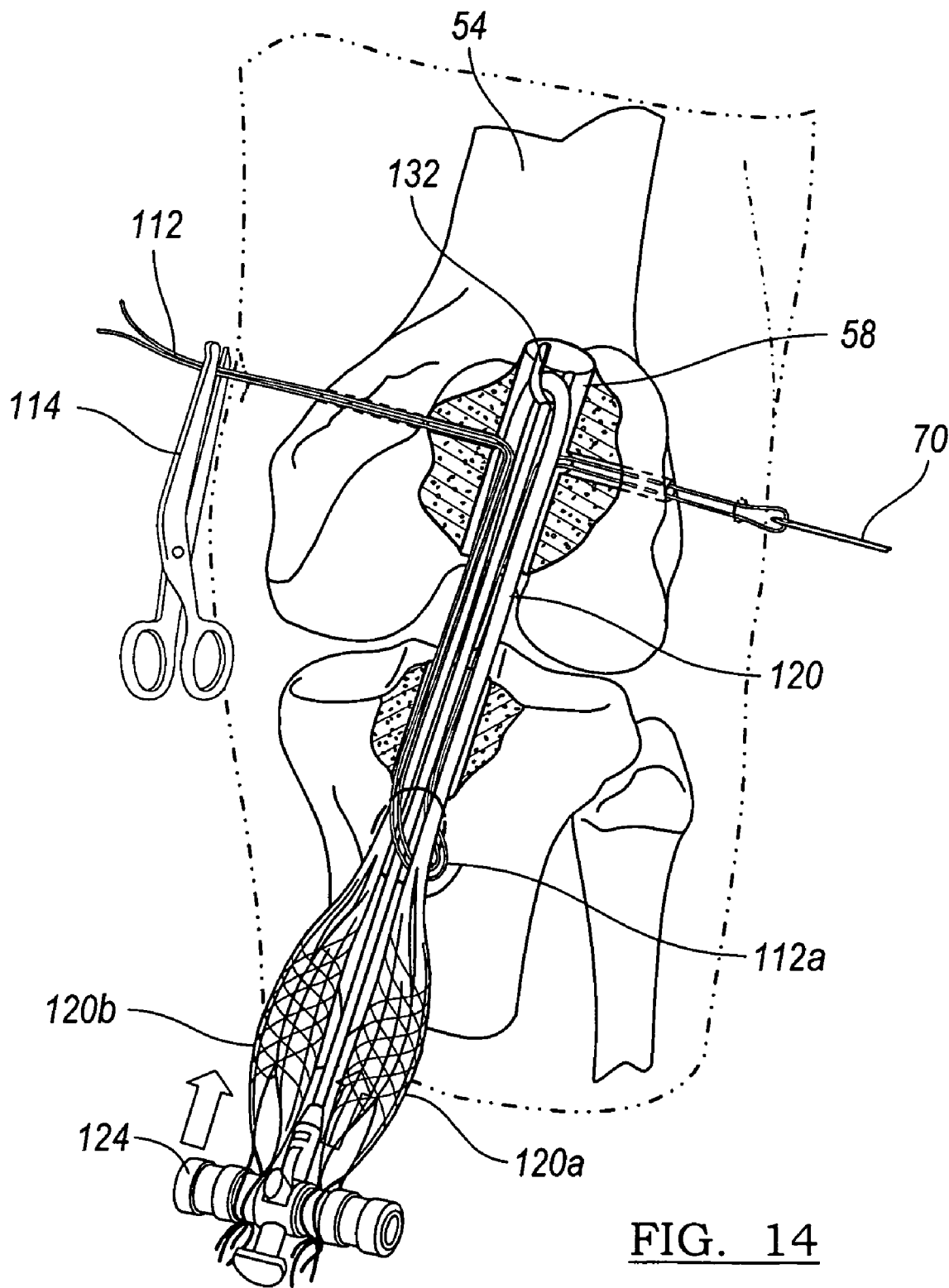
FIG. 14 is an environmental perspective view of an apparatus according to various embodiments positioned relative to a knee with a pin alignment suture through the femur and a graft pusher in a second position relative to the femur.

Once the pin alignment suture 112 has been held in a selected position, such as with the clip 116, a soft tissue graft 120 can be interconnected with a positioning tool 124, as illustrated in FIG. 14. The soft tissue graft 120 can include any appropriate soft tissue, such as an allograft, a xenograft, an autograft, or combinations thereof. The soft tissue graft 120 can be formed or prepared in any appropriate manner. For example, ends of the soft tissue graft can be intertwined or sutured together with a graft suture 126. The intertwined end 128 of the soft tissue graft 120 are thereby held relative to one another for implantation of the soft tissue graft 120.

The positioning instrument 124 can include any appropriate mechanism to assist in positioning the soft tissue graft 120 in the tunnels 56, 58. For example, the positioning instrument 124 can include a positioning arm 128 and a T bar or handle 130. The positioning arm 128 can include a distal fork or graft engaging portion 132. The handle 130 can include any appropriate configuration to allow for interconnecting the sutures 126 therewith. Interconnecting the sutures 126 with the handle 130 can assist in holding the soft tissue 120 relative to the positioning instrument 124 for a selected period of time. It will be understood, however, that the fork 132 can be any appropriate portion and a fork is merely exemplary.

The soft tissue graft 120 can be sized in any appropriate manner. For example, the soft tissue graft 120 can include a dimension, a volume, a diameter, or the like that can substantially fill at least a portion of the femoral tunnel 58 or the tibial tunnel 56. It will be understood, however, that the soft tissue graft 120 can be formed in any appropriate size for achieving a selected result. The positioning instrument 124 allows the graft 120 to be positioned into the tunnel, such as allowing it to be substantially seated in the tibial tunnel 58 without the assistance of any other mechanisms. The graft positioning member 124 allows the graft 120 to be passed through the tunnels 56, 58 with ease by a user, such as a physician. The positioning member 124 also enables a size specific graft that is sized to fill the diameter of the tunnels 56, 58 to be moved into the tunnels. The tunnels 56, 58 can be formed to substantially match a dimension of the graft for various purposes such as initial fixation and bone ingrowth.

As discussed above, the positioning instrument 124 allows for pushing the soft tissue graft 120 into the tunnels 56, 58. Because the soft tissue graft 120 is pushed into the tunnels 56, 58, the soft tissue graft can be formed to substantially fill the tunnels so that a substantial force can be used push the soft tissue graft 120 into the tunnels 56, 58. It will be understood that the force used may not cut or otherwise deteriorate the graft 120, but the force may be substantial due to the positioning instrument 154.

Further, the tunnel is formed in the anatomy, such as the femoral tunnel 58 can be sized such that the tibia tunnel extends a selected distance past the transverse tunnel 72. The transverse tunnel 72 can be formed relative to the femoral tunnel 58 such that there is a head room or distance that is formed by the femoral tunnel 58 that is past or extends past the transverse tunnel 72. As discussed above, the guide bit 70 generally assists in positioning the implant 130 relative to the soft tissue graft 120 after the soft tissue graft 120 is in position in the femoral tunnel 56. Therefore, the soft tissue graft 120 can be pushed into the femoral tunnel 56 such a distance that the implant 120 does not substantially interact with or contact the soft tissue graft 120 as it is passed through the transverse tunnel 72 as discussed further herein. This can be provided for various reasons such as easing the positioning of the implant 130 relative to the soft tissue graft 120 and the femoral tunnel 56. Because the soft tissue graft 120 is substantially pushed past the transverse tunnel 72, the implant 130 can be easily and efficiently moved past and/or through the femoral tunnel 56 without substantially contacting the soft tissue graft 120 while moving the implant 130.

With reference to FIG. 14, once the graft 120 has been positioned in a selected location in the tibial tunnel 58, the clip 116 holding the pin alignment suture 112 at a selected location exterior to the femur 54 can be released. The pin placement suture 112 forms a loop 112a that is clipped with a clip 116. The loop 112a can be positioned relative to the soft tissue graft 120 such that the positioning suture 112 can be placed between the portions of the soft tissue graft 120.

Figure 15:
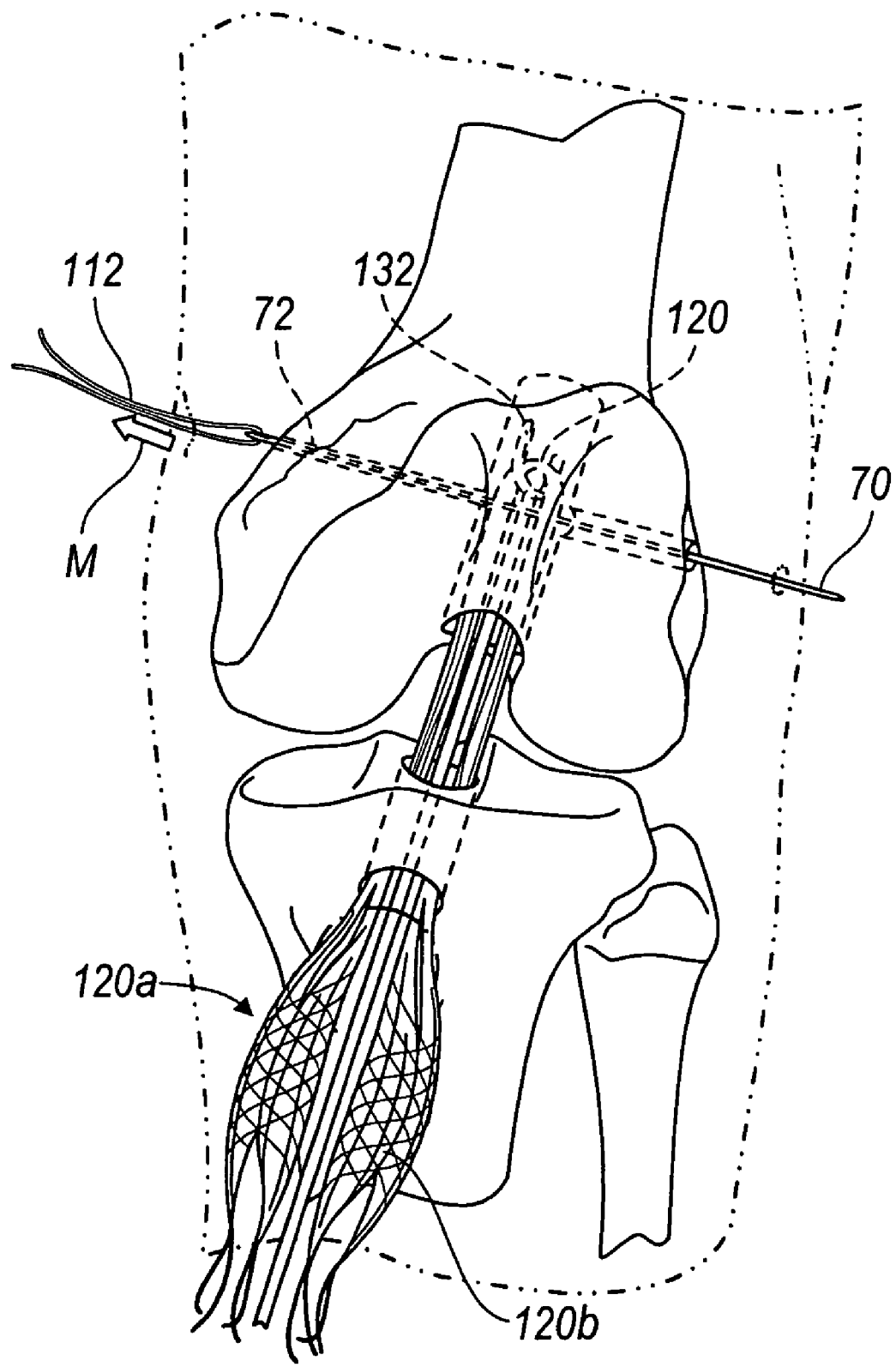
FIG. 15 is an environmental perspective view of an apparatus according to various embodiments positioned relative to a knee with a pin alignment suture through the femur and the graft in a position relative to the femur.

With reference to FIG. 15, the soft tissue graft 120 can include a first or anterior portion 120a and the second or posterior portion 120b. The suture positioning loop 112a can be positioned between and/or below the two portions 120a, 120b of the soft tissue graft 120. Once the loop 112a is positioned relative to, such as below, the portions of the soft tissue graft 120, the positioning suture 112 can be held within the femoral tunnel 58 such as with the clamping member 114. Regardless, the pin alignment suture 112 can be formed or made taut within the femoral tunnel by moving it generally in the direction of the arrow M. It will be understood that the graft positioning instrument 124 can be disconnected from the soft tissue graft 120 to allow for the loop 112a to be passed between the portions 120a, 120b of the soft tissue graft 120.

The pin alignment suture 112 can be used to move the drill point 70 through at least a portion of the transverse femoral tunnel 72. The drill point 70 can also act as an implant alignment or positioning mechanism. Therefore, the drill point 70 is generally pulled under the graft 120 such as between the two portions 120a, 120b. The pin positioning suture 112 assists in pulling the drill point beneath the graft 120.

Figure 16:
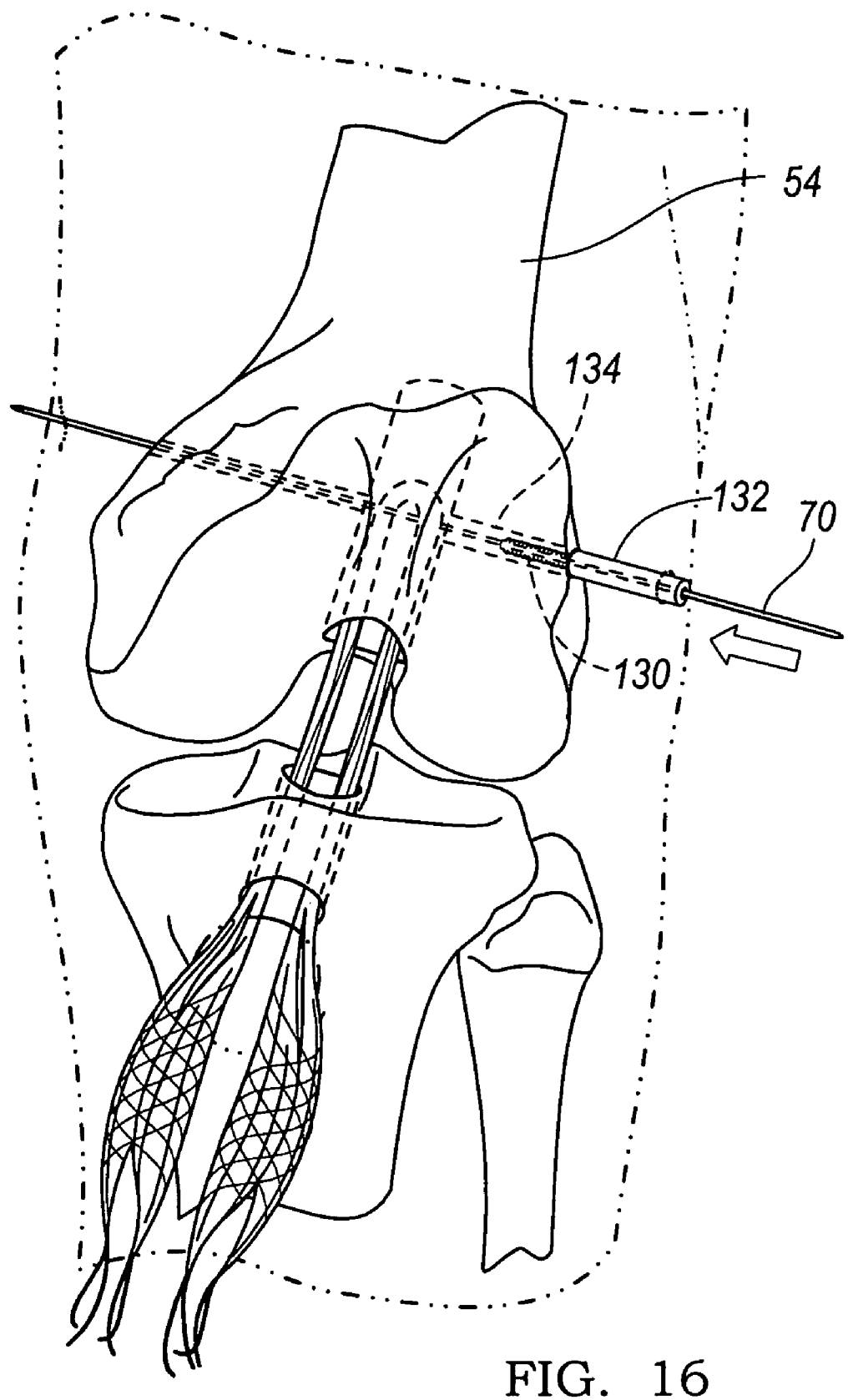
FIG. 16 is an environmental perspective view of an apparatus according to various embodiments positioned relative to a knee with a pin alignment suture through the femur and the graft in a position relative to the femur and aligning an implant according to various embodiments.

With reference to FIG. 16, an implant 130 can be passed over the guide wire drill point 70. The implant 130 may be similar to the implant 84 for holding the soft tissue graft 120 relative to the femur 54. The implant 30, however, can include other portions. For example, the implant 130 may be cannulated such that it is able to pass over the drill point 70. Further, it may include a proximal threaded or bone engagement portion 132 and a distal tunnel engagement portion 134. The implant 130 can include a tapered structure such that it is able to pass under the graft 120 in a non-binding manner.

Figure 17:
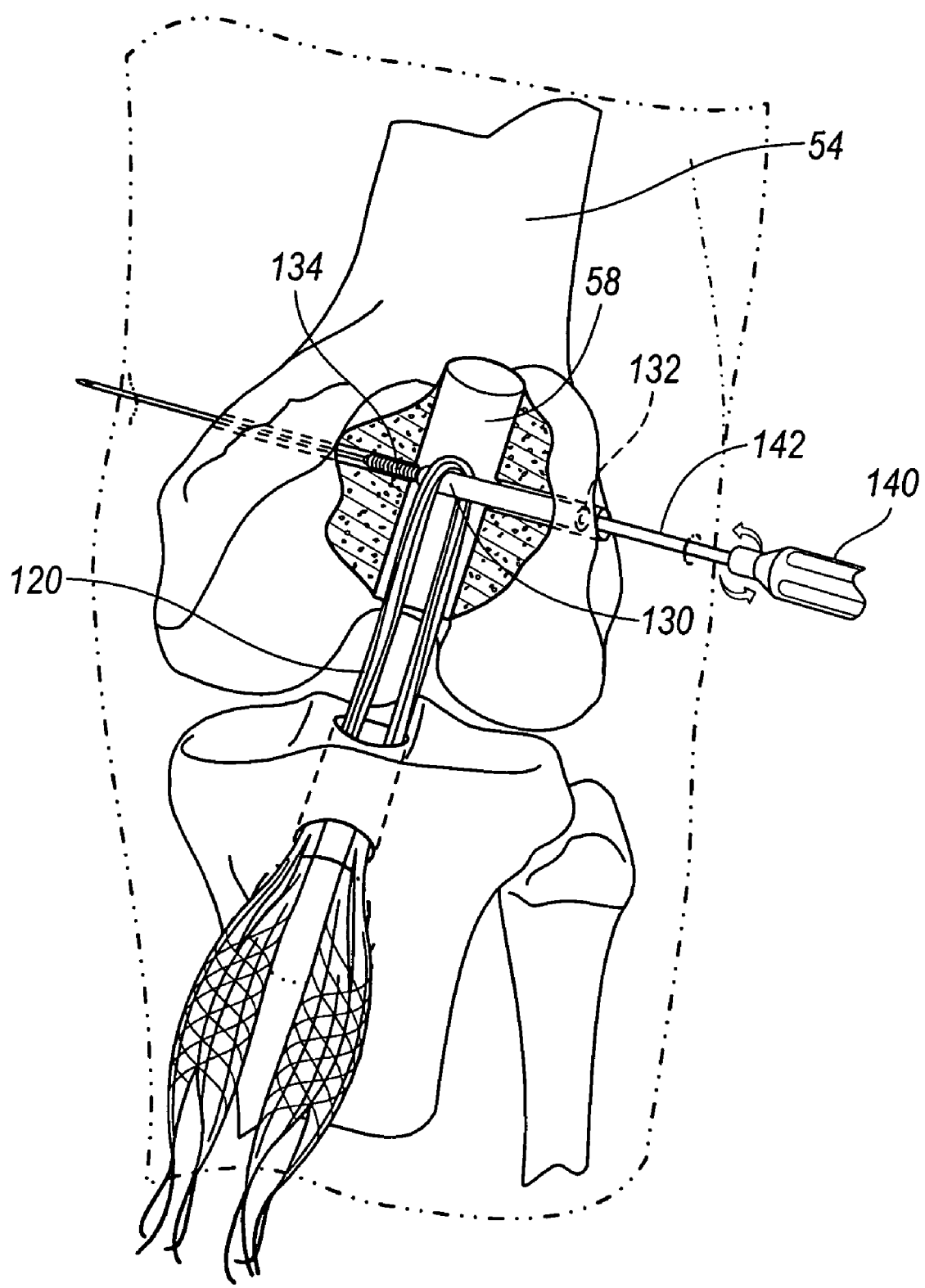
FIG. 17 is an environmental perspective view of an apparatus according to various embodiments positioned relative to a knee with a pin alignment suture through the femur and the graft in a position relative to the femur and fixing an implant according to various embodiments.

The implant 130 may pass over the drill wire 70 in any appropriate manner such as with a tool, annularly or the like. Once the implant 130 is positioned relative to the femur 54, it can be fixed relative to the femur 54 in any appropriate manner. For example, a driving tool 140 may engage a portion of the implant 130 such as a tool engaging portion of the implant 130, as illustrated in FIG. 17. The tool engaging portion of the implant 130 can include an interior tool engaging portion such that the bone engaging portion 132 can extend substantially to an end of the implant 130. The bone engaging portion 132 can include threads such that operation of the tool 140 acts to rotate the implant 130 so the threads are able to engage the femur 54.

The implant 130 can include a main body portion that engages the enlarged transverse tunnel 73 while the distal portion 134 engages the unenlarged transverse tunnel 72. It will be understood, however, that the implant 130 can be formed in any appropriate manner to engage the femur in any appropriate manner to allow fixation of the graft 120 thereto.

The tool 140 can include a measurement sleeve 142 that is able to assist in determining an appropriate driven distance of the implant 130. The measuring sleeve 142 can include demarcations that allow it to be used to determine whether the implant 130 has been driven an appropriate distance into the femur 54. The demarcations on the sleeve 142 can be referenced to the demarcations on the sizing member 100 to ensure that the implant 130 is positioned relative to the femoral tunnel 58 in any appropriate manner to hold the graft 120.

Once the implant 130 has been positioned relative to the femur 54 through the transverse tunnel 72, 73, the soft tissue graft 120 can be fixed to the tibia 52 in any appropriate manner such as that described above. For example, the implant 90 can be used to fix the proximal end of the soft tissue relative to the tibia 52, as illustrated in FIG. 9.

It will be understood that any appropriate implants may be used for the various implants described herein. For example, the AXL™ cross pin produced by Arthrotek, Inc. of Warsaw, Ind. can be used by the implant 130. Further, the tibial fixation implant can be any appropriate implant such as the Bone Mulch™ Screw or LactoSorb™ Cross Pin produced by Arthrotek, Inc. of Indiana, U.S.A. or the Trans Fix™ implant by Arthrex, Inc.

It will be understood that the method described herein can be used to position a soft tissue graft relative to any appropriate portion of the anatomy. Although replacement of a soft tissue portion in a femur 54 and a tibia 52 have been described, interconnection of any appropriate bone portions can be formed with the various instruments and methods taught herein.

The teachings herein are merely exemplary in nature and, thus, variations that do not depart from the gist thereof are intended to be within the scope of the teachings. Such variations are not to be regarded as a departure from the spirit and scope of the teachings.

What is claimed is:

1. A method of positioning a soft tissue graft into a bore formed in a bone, comprising:
    forming a loop of soft tissue;
    forming a first bore in a first bone;
    forming a second bore in a second bone, and a third bore in the second bone at an angle to the second bore;
    passing a suture into the third bore such that a portion of the suture is disposed outside at least an end of the third bore;
    withdrawing another portion of the suture through the second bore and the first bore;
    pushing the loop of soft tissue graft into the first bore formed in the first bone and into the second bore formed in the second bone;
    pulling at least one portion of the suture outside of the third bore to draw the withdrawn portion through the first bore and into the second bore to position the suture below the loop of soft tissue in the second bore after pushing the soft tissue graft into the second bore;
    coupling the suture to an implant guiding member and further pulling the suture to draw the implant guiding member into the third bore and under the loop of soft tissue; and
    fixing the soft tissue graft to the bone by guiding an implant with the implant guiding member.

2. The method of claim 1, further comprising:
    fixing the soft tissue graft to the first bone.

3. A method of positioning a soft tissue graft into a bore formed in a bone, comprising:
    forming a first bore in a first bone;
    forming a second bore in a second bone and a third bore in the second bone at an angle relative to the second bore such that the third bore intersects the second bore;
    positioning a flexible member through the third bore such that portions of the flexible member are disposed outside of each end of the third bore;
    withdrawing another portion of the flexible member through the second bore and the first bore;
    engaging the soft tissue graft portion and holding the soft tissue graft in a selected orientation with a graft engaging portion;
    allowing the soft tissue graft to lie between two portions of a fork of the graft engaging portion;
    grasping a handle by a user intraoperatively;
    manipulating the engaged soft tissue graft portion via a member interconnecting said graft engaging portion and said graspable handle so that movement of said graspable handle translates into movement of said graft engaging portion;
    pushing of said handle to move the soft tissue graft into the first bore and then into the second bore;
    pulling at least one portion of the flexible member outside of the third bore to draw the withdrawn portion through the first bore and into the second bore to position the flexible member below the soft tissue graft in the second bore after pushing the soft tissue graft into the second bore;
    coupling said flexible member to an implant guiding member and further pulling the flexible member to draw the implant guiding member into the third bore and under the soft tissue graft;
    fixing the soft tissue graft to the bone by guiding an implant with the implant guiding member; and
    engaging a suture in the handle, wherein a suture fixed to a portion of the soft tissue graft is engaged on the handle.

4. The method of claim 3, further comprising:
    pushing a specifically sized soft tissue graft into the bore with at least one of the graft engaging portion, the member, or combinations thereof.

5. A method of positioning a soft tissue graft into a bore formed in a bone, comprising:
    forming a first bore in a first bone;
    forming a second bore in a second bone;
    forming a third bore in the second bone at an angle relative to said second bore;
    positioning a suture through the third bore such that a portion of the suture is disposed and temporarily retained outside of each end of the third bore;
    withdrawing another portion of the suture through the second bore and then the first bore, and temporarily retaining the withdrawn portion outside of the first bore;
    positioning the soft tissue graft over a portion of a pushing instrument;
    fixing an end of the soft tissue graft to a graspable portion of the pushing instrument;
    pushing the soft tissue graft through the first bore formed in the first bone with the pushing instrument; and
    pushing the soft tissue graft into the second bore after pushing the soft tissue graft through the first bore;
    pulling at least one portion of the suture outside of the third bore to draw the withdrawn portion through the first bore and into the second bore to position the suture below the soft tissue graft in the second bore after pushing the soft tissue graft into the second bore;
    passing an implant through said third bore to fix the soft tissue graft to the second bone after the soft tissue graft has been pushed into an end of the second bore; and
    guiding said implant with an implant guiding member, wherein said guiding includes further pulling the suture to draw the implant guiding member into the third bore and under the soft tissue graft.

6. The method of claim 5, further comprising:
    fixing the soft tissue graft to the first bone.

7. A method of positioning a soft tissue graft into a bore formed in a bone, comprising:
    forming a tibial tunnel in a tibia;
    forming a first femoral tunnel in a femur;
    forming a second femoral tunnel in the femur at an angle relative to said first tunnel;
    positioning a suture through the second femoral tunnel, the suture being coupled to an implant guiding member outside of one end of the second femoral tunnel and retained outside the second femoral tunnel at an opposite end of the second femoral tunnel;
    withdrawing a portion of the suture through the first femoral tunnel and the tibial tunnel, and temporarily retaining the withdrawn portion outside the tibial tunnel;
    forming a loop of soft tissue;
    positioning the loop of soft tissue on a soft tissue pusher instrument;
    pushing the loop of soft tissue graft into the tibial tunnel with the soft tissue pusher instrument;
    pushing the soft tissue graft into the first femoral tunnel;

pulling at least one portion of the suture disposed outside of the second femoral tunnel to draw the withdrawn portion through the tibial tunnel and into the first femoral tunnel to position the suture below the loop of soft tissue pushed into the first femoral tunnel;

passing an implant through said second femoral tunnel and under the loop of soft tissue to fix the soft tissue graft to the femur after the soft tissue graft has been pushed into an end of the first femoral tunnel, wherein the soft tissue implant engages the implant and is held relative to the second femoral tunnel within the femur; and guiding said implant with an implant guiding member, wherein said guiding includes further pulling the suture to draw the implant guide member into the second femoral tunnel and under the loop of soft tissue.

8. The method of claim 7, further comprising:
fixing the soft tissue graft to the tibia.

9. The method of claim 7, wherein the soft tissue pusher instrument and the soft tissue graft are sized to fit within the tibial tunnel and the first femoral tunnel without binding.

10. The method of claim 1, wherein forming a third bore includes forming a third bore through the second bone and at an angle to the first bore.

11. The method of claim 1, wherein forming a second bore includes forming a second closed end bore in a second bone.

12. The method of claim 3, wherein the flexible member includes a suture.

13. The method of claim 3, wherein withdrawing another portion of the flexible member further includes temporarily retaining the withdrawn portion outside of the first bore.

14. The method of claim 13, further comprising retaining the withdrawn portion with a retention mechanism.

15. The method of claim 5, wherein pulling at least one portion of the suture outside of the third bore includes pulling both portions of the suture disposed outside of the third bore.

16. The method of claim 7, wherein the withdrawn suture portion forms a loop, and wherein the formed loop of soft tissue includes respective end portions, the loop portion of the suture being positioned between the soft tissue end portions and below the soft tissue loop portion.

17. The method of claim 7, further comprising maintaining the loop portion of the suture outside the tibial tunnel while pushing the loop of soft tissue graft into the tibial tunnel and first femoral tunnel.

18. The method of claim 7, wherein the loop of soft tissue is pushed to a terminal end of the first femoral tunnel that is beyond the second femoral tunnel such that the implant can be guided through the second and first femoral tunnels without substantially contacting the soft tissue implant.

19. The method of claim 7, wherein pulling at least one end of the suture includes pulling the retained end while maintaining the guiding member outside the second femoral tunnel.

20. A method of positioning a soft tissue graft into a bore formed in a bone, comprising:
forming a first bore in the bone;
forming a second bore in the bone at an angle to and intersecting the first bore;
passing a suture into the second bore and out of the first bore such that the suture forms a loop outside of the first bore;
positioning a loop of soft tissue over the suture loop;
pushing the looped soft tissue into the first bore;
positioning the suture below the looped tissue in the first bore;
coupling a portion of the suture to an implant guide member outside of one end of the second bore and retaining another portion of the suture outside of an opposite end of the second bore;
pulling the suture to draw the implant guide member into the second bore and under the loop of soft tissue; and
fixing the soft tissue to the bone by guiding an implant with the implant guide member.

21. The method of claim 20, further comprising maintaining the suture loop outside of the first bore while pushing the looped soft tissue into the first bore.

22. The method of claim 20, wherein forming the second bore includes forming the second bore through the bone at an angle to and intersecting the first bore.

23. The method of claim 20, wherein positioning the suture below the looped tissue in the first bore includes pulling both portions of the suture disposed outside of the second bore to draw the suture loop into the first bore and position the suture below the looped tissue in the first bore.

24. The method of claim 20, wherein pushing the looped soft tissue into the first bore includes pushing the looped soft tissue into the first bore to a terminal end of the first bore, the terminal end of the first bore extending beyond the intersection of the second bore with the first bore.

* * * * *